United States Patent [19]

Becker et al.

[11] Patent Number: 5,055,569

[45] Date of Patent: Oct. 8, 1991

[54] N-(6)-SUBSTITUTED ADENOSINE COMPOUNDS

[75] Inventors: Daniel P. Becker, Glenview; Paul W. Collins, Deerfield; Daniel L. Flynn, Mundelein, all of Ill.

[73] Assignee: G. D. Searle & Co., Chicago, Ill.

[21] Appl. No.: 423,923

[22] Filed: Oct. 19, 1989

[51] Int. Cl.$^5$ .................... C07H 19/06; A61K 31/70
[52] U.S. Cl. ................................................ 536/26
[58] Field of Search ........................... 536/26; 514/46

[56] References Cited

U.S. PATENT DOCUMENTS

| | | | |
|---|---|---|---|
| 3,551,409 | 12/1970 | Kampe et al. | 260/211.5 |
| 3,851,056 | 11/1974 | Stork et al. | 424/180 |
| 3,901,876 | 8/1975 | Vorbruggen et al. | 260/211.5 R |
| 4,340,730 | 7/1982 | Henderson et al. | 536/26 |
| 4,464,361 | 8/1984 | Ohki et al. | 424/180 |
| 4,582,823 | 4/1986 | Heffner et al. | 514/46 |
| 4,593,019 | 6/1986 | Bristol et al. | 514/46 |
| 4,600,707 | 7/1986 | Patt | 514/46 |
| 4,614,732 | 9/1986 | Hamilton et al. | 514/46 |
| 4,616,003 | 10/1986 | Hamilton et al. | 514/46 |
| 4,626,526 | 12/1986 | Bristol | 514/46 |
| 4,663,313 | 5/1987 | Bristol et al. | 514/46 |
| 4,673,670 | 6/1987 | Hamilton et al. | 514/46 |
| 4,683,223 | 7/1987 | Trivedi | 514/46 |
| 4,704,381 | 11/1987 | Schaumann et al. | 514/46 |
| 4,714,697 | 12/1987 | Trivedi | 514/46 |
| 4,738,954 | 4/1988 | Hamilton et al. | 514/46 |
| 4,755,594 | 7/1988 | Bridges et al. | 536/26 |
| 4,764,506 | 8/1988 | Patt | 514/46 |
| 4,767,747 | 8/1988 | Hamilton et al. | 514/46 |
| 4,791,103 | 12/1988 | Trivedi et al. | 514/46 |
| 5,636,493 | 1/1987 | Patt | 514/46 |

FOREIGN PATENT DOCUMENTS

| | | |
|---|---|---|
| 0061001 | 9/1982 | European Pat. Off. . |
| 47-71985 | 3/1974 | Japan ............... 16 E/611.2 |

WO 88/03147  5/1988  PCT Int'l Appl. .
WO 88/03148  5/1988  PCT Int'l Appl. .

OTHER PUBLICATIONS

Kikugawa et al., Platelet Aggregation etc., J. Med. Chem. 16, 358–364 01/73.
Morr et al., Aminonucleosides. Part IX. etc., J. Chem. Research, (S) 90–91, 01/81.
Dutta et al., Synthesis and Biological Activities of Some etc., J. Carbohydrates.Nucleosides.Nucleotides 5(1), 47–57, 01/78.
Baer et al., Effects of Amino and Ammonio Derivatives of etc., Can. J. Physiol. Pharmacol. 63(1), 58–61, 01/85.

Primary Examiner—John W. Rollins
Attorney, Agent, or Firm—Roger A. Williams; Paul D. Matukaitis

[57] ABSTRACT

The present invention relates to N-(6)-substituted adenosine compounds of the formula

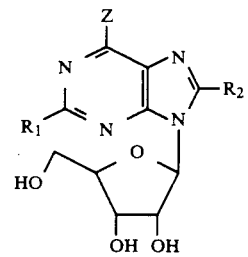

or a pharmaceutically acceptable salt thereof, wherein Z is an amine and $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl or phenyl.

45 Claims, No Drawings

N-(6)-SUBSTITUTED ADENOSINE COMPOUNDS

BACKGROUND OF THE INVENTION

The invention herein is directed to compounds which can be useful in the treatment of gastrointestinal motility disorders of mammals by administering to the mammal in need thereof a therapeutically effective amount of a compound disclosed herein or a pharmaceutically acceptable salt thereof. The compounds used herein are adenosine derived compounds. The compounds can be used to treat gastrointestinal motility disorders such as gastroesophageal reflux, delayed gastric emptying, irritable bowel syndrome, and the like. The compounds disclosed herein have been found to exhibit gastrointestinal prokinetic activity and are therefore, useful in treating gastrointestinal motility disorders.

Certain N-(6)-substituted adenosine compounds have heretofore been found to be useful as cardiovascular/-coronary vasodilators, platelet aggregation inhibitors, growth regulators and anti neoplastic agents. Such compounds have demonstrated biological activity, such as smooth muscle contractility and adenylate cyclase activity, anti hypertensive activity, anti allergic activity, anti-lipolytic activity and anti hyper-lipaemic activity.

Japanese patent 49/30396 of Kohjin Company Limited; Japanese patent 49/30395, also of Kohjin Company Limited; U.S. Pat. No. 3,901,876 of Schering; U.S. Pat. No. 3,551,409 of Boehringer Mannheim; U.S. Pat. No. 4,464,361 of Fujisawa Pharmaceutical Company Limited; and West German Patent 2139107 of Merck Patent GmbH all disclose utility for various adenosine derivatives as cardiovascular agents or coronary vasodilators, anti hypertensive agents, bradycardiac agents or central nervous system agents.

U.S. Pat. No. 4,340,730 of G. D. Searle & Co. discloses anti-hypertensive activity for certain adenosine derivatives.

K Kikugawa, et al. disclose in *J. Med. Chem.* (1973) 16, 358 (1973) adenosine derivatives which act as platelet aggregation inhibitors.

S. P. Dutta, et al. disclose in *J. Carbohydrates, Nucleosides, Nucleotides,* 5, 47 (1978) that certain adenosine derivatives have utility as growth regulators, anti-neoplastic agents and exhibit cytokinin activity.

H. P. Baer has found that certain adenosine derivatives exhibit smooth muscle contractility and adenylate cyclase activity in in vitro studies, *Can. J. of Physiology Pharmacol.* 63, 58 (1985).

U.S. Pat. No. 4,704,381 of Boehringer Mannheim discloses certain adenosine derivatives that exhibit anti allergic activity and which, therefore, can be used as anti-allergic agents.

European patent 0061001A1 of Yamasa Shoyu discloses that certain adenosine derivatives exhibit anti allergic activity.

U.S. Pat. No. 3,851,056 of Boehringer Mannheim discloses certain adenosine derivatives which exhibit anti lipolytic and anti-hyperlipaemic activity.

SUMMARY OF THE INVENTION

The invention herein is directed to compounds of the formula

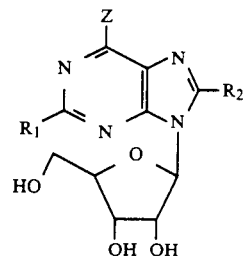

or a pharmaceutically acceptable salt thereof, wherein Z can be:

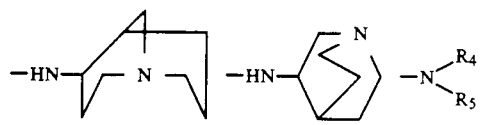

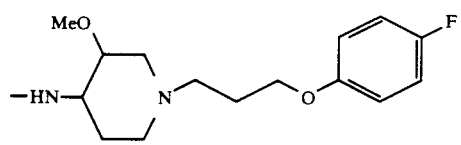

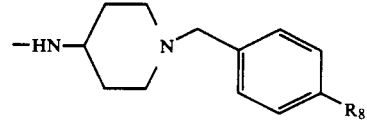

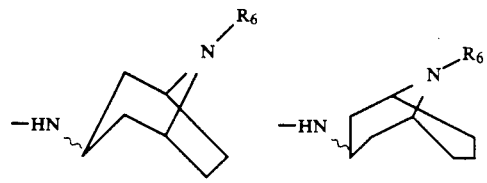

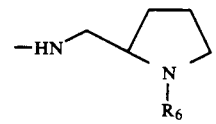

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl, or phenyl; wherein $R_4$ can be hydrogen or alkyl wherein $R_5$ is —X—Y wherein X can be a straight chain, branched chain or cyclic alkylene from 1 to 10 carbon atoms, and wherein Y can be optionally substituted imidazol-1 yl, imidazol-2-yl, pyrrolinyl, pyrrolidinyl, piperidinyl, triazolyl,

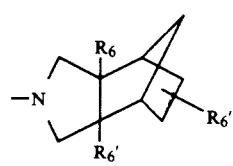

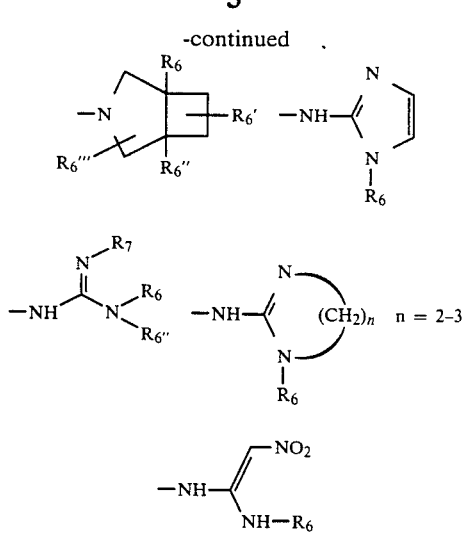

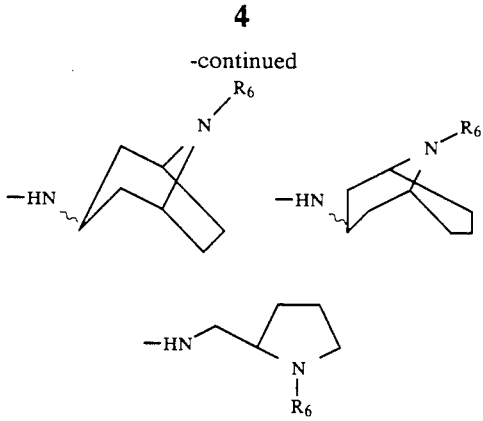

wherein $R_8$ can be hydrogen, alkyl, aralkyl, aryl or acyl; and wherein $R_6$ can independently be hydrogen, alkyl, aralkyl, phenyl, and optionally substituted phenyl and aralkyl; wherein $R_7$ can be hydrogen, alkyl, aralkyl, phenyl, cyano and nitro; and wherein n can be 2 or 3.

The term $R_6$ is used herein with or without primes. It is intended herein that the use of primes indicates that $R_6$ may or may not be the same group but will remain one of the acceptable defined groups.

DETAILED DESCRIPTION OF THE INVENTION

The invention herein is directed to compounds of the formula:

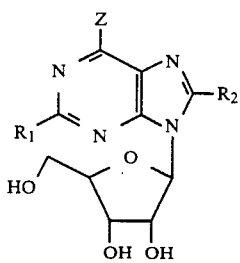

wherein Z can be:

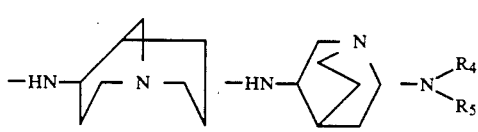

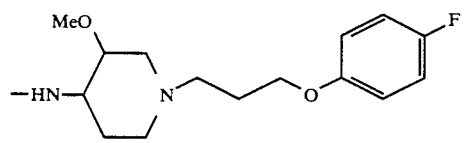

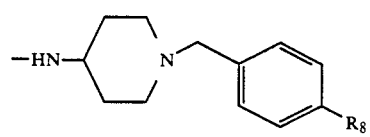

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl, or phenyl; wherein $R_4$ can be hydrogen or alkyl; wherein $R_5$ is —X—Y; wherein X can be a straight chain, branched chain or cyclic alkylene from 1 to 10 carbon atoms; and wherein Y can be optionally substituted imidazol-1-yl, imidazol-2-yl, pyrrolinyl, pyrrolidinyl, piperidinyl, triazolyl,

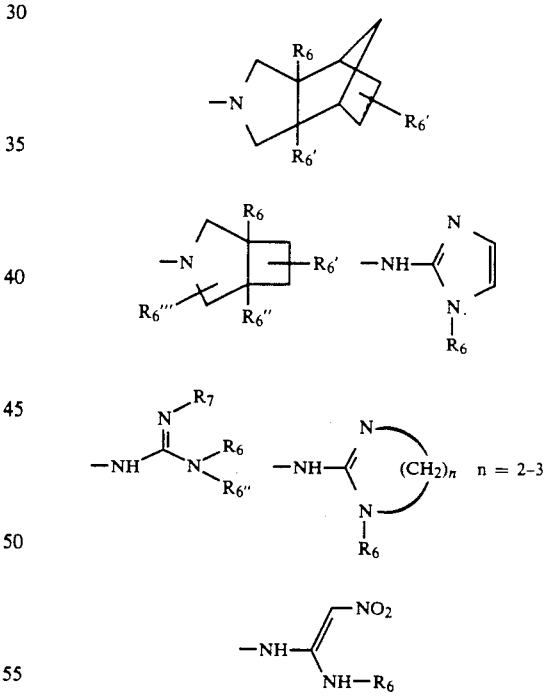

wherein $R_8$ can be hydrogen, alkyl, aralkyl, aryl or acyl; and wherein $R_6$ can independently be hydrogen, alkyl, aralkyl, phenyl, and optionally substituted phenyl and aralkyl; wherein $R_7$ can be hydrogen, alkyl, aralkyl, phenyl, cyano, and nitro; wherein n can be 2 or 3; or a pharmaceutically acceptable salt thereof.

A more preferred method of treating gastrointestinal motility disorders is performed by administering to a mammal in need of such treatment a therapeutically effective amount of a compound of the formula:

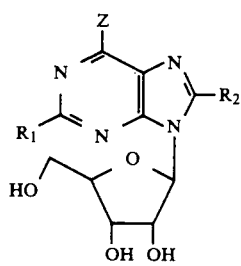

wherein Z can be:

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl, or phenyl; wherein $R_4$ can be hydrogen or alkyl; and wherein $R_5$ is —X—Y; wherein X can be a straight chain, branched chain or cyclic alkylene from 1 to 10 carbon atoms; and wherein Y can be optionally substituted imidazol-1-yl, imidazol-2-yl, pyrrolinyl, pyrrolidinyl, peperidinyl, triazolyl,

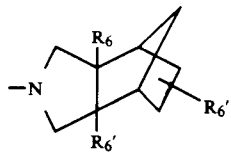

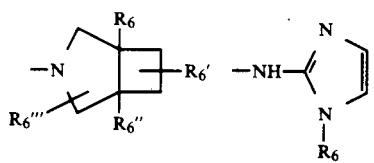

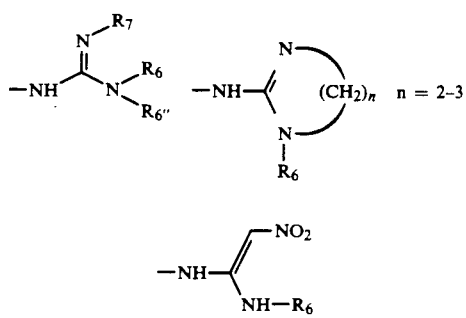

wherein $R_6$ can independently be hydrogen, alkyl, aralkyl, phenyl, and optionally substituted phenyl and aralkyl; wherein R can be hydrogen, alkyl, aralkyl, phenyl, cyano, and nitro; wherein n can be 2 or 3; or a pharmaceutically acceptable salt thereof.

Another preferred group of compounds of the formula:

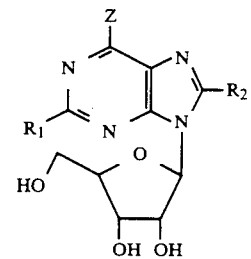

wherein Z can be:

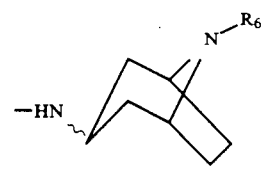

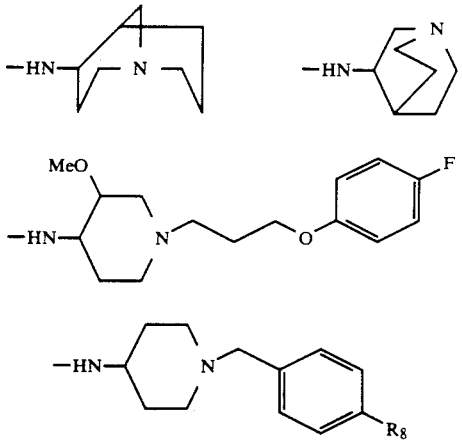

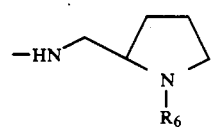

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl, or phenyl; wherein $R_8$ can be hydrogen, alkyl, aralkyl, aryl or acyl; and wherein $R_6$ can be hydrogen, alkyl, aralkyl, phenyl, and optionally substituted phenyl and aralkyl; or a pharmaceutically acceptable salt thereof.

In the structures or formulas herein the solid triangular bond representation represents a bond extending outwardly from the plane of the paper on which it is drawn. In a similar manner, the series of dashes of decreasing length are used to represent a bond extending below the plane of the paper on which the structure is drawn.

In the structural formulas, a dashed line represents an optional bond between the two atoms. For example, the solid and dashed lines (a straight line and above it a series of dashes of the same length) indicate that the bond can be either a single bond or double bond between the two atoms.

The compounds herein are not limited to any particular stereochemical configuration at the N-(6)-side chain; i.e., for Z. Both cis and trans isomers, where possible, are within the scope of the invention and can be used in the treatment of gastrointestinal motility disorders. In addition, geometric isomers, diastereomers and enantiomers (except for the D-ribose moiety) are also within the scope of the invention herein.

The term "lower alkyl" as used herein means straight or branched chain alkyls having from 1 to 6 carbon atoms.

The term "aryl" as used herein describes phenyl or substituted phenyl.

For the purpose herein the term "thiophenoxy" is used to mean the group having the structure:

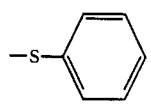

The term "pharmaceutically acceptable salts" includes acid addition salts with conventional acids including mineral acids such as hydrochloric, hydrobromic, phosphoric, sulfuric, and organic acids such as ethanesulfonic, benzenesulfonic, p-toluenesulfonic, succinic, citric, tartaric, lactic, acetic acid and the like. (See for example, "Pharmaceutical Salts," *J. Pharm. Sci* (1977)66(1):1–19.) The pharmaceutically acceptable salts of the compounds also include quaternary ammonium salts. Examples of such salts include salts with compounds such as $R_3$—Y wherein $R_3$ is $C_{1-6}$ alkyl, phenyl-$C_{1-6}$ alkyl, or $C_{5-7}$ cycloalkyl, and Y is an anion of an acid. Suitable examples of $R_3$ include methyl, ethyl and n- and iso propyl; and benzyl and phenyl ethyl. Suitable examples of Y include the halides such as chloride, bromide and iodide.

The acid addition salts can be prepared either by dissolving the free base in aqueous or aqueous alcohol solution or other suitable solvent containing the appropriate acid and isolating the salt by evaporating the solvent, or by reacting the free base and acid in an organic solvent, in which case the salt separates directly or can be obtained by concentration of the solution.

Quaternary ammonium salts can be prepared by reaction of the free base with an appropriate organohalide as described above. The reaction can be carried out in a solvent, such as acetone, methanol, ethanol or dimethylformamide at ambient or elevated temperature with or without pressure.

N-oxides of the compound can be formed conventionally. N-oxides of the nitrogen atom of the cyclic ring system are produced by reaction of a compound with an organic peracid, such as m-chloroperbenzoic acid in, for example, a chlorinated hydrocarbon solvent at below ambient temperature.

The compounds disclosed herein can be used in the treatment of mammals exhibiting gastrointestinal disorders such as gastroesophageal reflux, delayed gastric emptying, irritable bowel syndrome, and the like.

The treatment can be practiced by administering one of the noted compounds to a mammal in need of such a treatment in a therapeutically effective amount. The compounds can be administered in such oral dosage forms as tablets, capsules, soft gels, pills, powders, granules, elixers, or syrups. The compounds can be administered intravascularly, intraperitoneally, subcutaneously, intramuscularly, or topically, using forms known to the pharmaceutical art. In general, the preferred form of administration is oral or in such a manner so as to localize the prokinetic agent to the gastrointestinal tract. For example, it is possible to administer the compounds via suppository.

For the oral administration of the compounds herein, the compounds are administered in admixture with suitable pharmaceutical diluents, excipients, or carriers (collectively referred to herein as "carriers") suitably selected with respect to the intended form of administration, that is, oral tablets, capsules, soft gels, elixirs, syrups, drops, and the like, and consistent with conventional pharmaceutical practices.

For example, for oral administration in the form of tablets or capsules, the active drug components can be combined with any oral non toxic pharmaceutically acceptable inert carrier, such as lactose, starch, sucrose, cellulose, magnesium stearate, dicalcium phosphate, calcium sulfate, mannitol, and the like, or various combinations thereof. For oral administration in liquid forms, such as in soft gels, elixirs, syrups, drops, and the like, the active drug components can be combined with any oral, non-toxic pharmaceutically acceptable inert carrier, such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, carboxyethylcellulose, polyethylene glycol, and waxes, or combinations thereof. Lubricants for use in these dosage forms include boric acid, sodium benzoate, sodium acetate, sodium chloride, and the like, or combinations thereof. Disintegrating agents include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, intramuscular, suppository or aerosol administration, active drug components can be combined with a suitable carrier such as water, saline, aqueous dextrose, and the like. Regardless of the route of administration selected, the compounds described as useful in the method herein can be formulated into pharmaceutically acceptable dosage forms by conventional methods known to those skilled in the art. The compounds can be formulated using pharmacologically acceptable acid addition salts. Moreover, the compounds or their salts can be used in a suitable hydrated form.

Regardless of the route of administration selected, a non toxic but therapeutically effective quantity of one or more compounds disclosed herein is employed. The dosage regimen for preventing or treating gastrointestinal motility disorders with the compounds is selected in accordance with a variety of factors, including disorder type, age, weight, sex, and medical condition of the patient, the severity of the gastrointestinal motility disorder, the route of administration, and the particular compound employed in the treatment. A physician or veterinarian of ordinary skill can readily determine and prescribe the effective amount of the compound required to prevent or arrest the progress of the condition. In so proceeding, the physician or veterinarian can employ relatively low doses at first and subsequently increase the dose until a maximum response is obtained The compounds herein can be prepared according to the reaction schemes set forth herein.

The following Reaction Scheme A shows the reaction sequence for preparing 6-N-substituted adenosine derivatives.

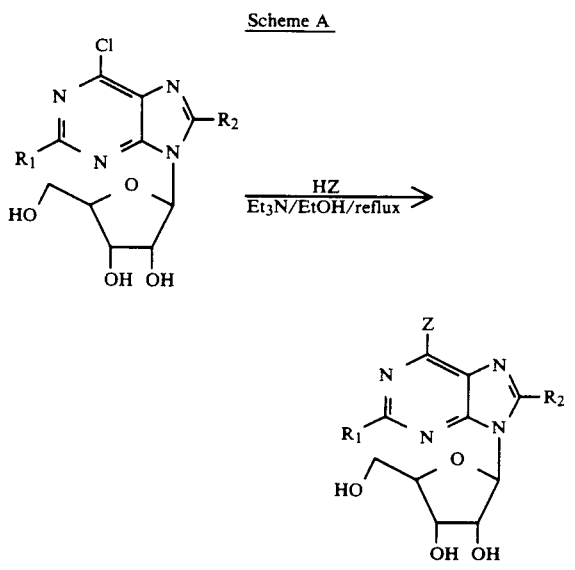

As illustrated in Scheme A, 6-chloropurine riboside is reacted with a suitable amine (HZ, wherein Z is as described above) to produce the adenosine derivative product. The reaction is conducted in a mixture of triethylamine and ethanol and is heated and refluxed to provide the adenosine derivative product.

The following examples are provided to illustrate the preparation of the adenosine derivative products useful herein using the reaction sequence shown in Scheme A. These examples, as well as all examples herein, are given by way of illustration only and are not to be construed as limiting the invention, either in spirit or scope, as many modifications, both in materials and methods, will be apparent from this disclosure to those skilled in the art. In these examples, temperatures are given in degrees Celsius (° C.) and quantities of materials in grams and milliliters unless otherwise noted.

EXAMPLE 1

N-[1-(phenylmethyl)-4-piperidinyl]adenosine

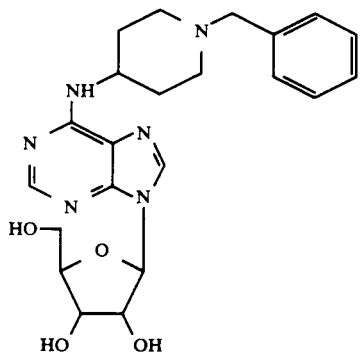

A suspension of 6-chloropurine rgboside (1.5 g, 5.2 mmole) in absolute ethanol (20 ml) was formed. To this suspension was added 4-amino-1-benzyl piperidine (1.08 g, 5.7 mmol) (commercially available) plus triethylamine (0.72 g, 7.2 mmol). The reaction mixture was heated under reflux for 88 hours. The reaction mixture was cooled to room temperature and the solvent was removed in vacuo. The resulting residue was chromatographed on silica gel eluting with an eluent consisting of 12 parts ammonia saturated ethanol [EtOH(NH$_3$)] and 88 parts dichloromethane which yielded 1.87 g (82% yield) of the title product.

Recrystallization from ether/methanol gave rosettes having a melting point of 176°-182° C.

MS: Calculated for $C_{22}H_{28}N_6O_4$, 441; found 441.

Combustion analysis for $C_{22}H_{28}N_6O_4$: Calculated: C, 59.99; H, 6.41; N, 19.08. Found: C, 59.70; H, 6.46; and N, 19.08.

EXAMPLE 2

N-[2-(1-pyrrolidinyl)ethyl]adenosine, monohydrochloride

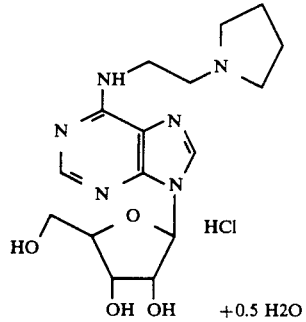

The experiment of Example 1 was repeated in every essential detail with the following exceptions. The suspension of 6-chloropurine riboside was formed using 1.80 g (6.3 mmol) in 12 ml of absolute ethanol. 1-(2-Aminoethyl) pyrrolidine (commercially available) was added in an amount of 0.93 g, (8.2 mmol). Triethylamine 0.95 g (9.4 mmol, 1.5 eq) was added and the reaction mixture refluxed for 68 hours. Concentration in vacuo gave a residue which was chromatographically separated on silica gel eluting with an eluent of 10 parts methanol, 90 parts dichloromethane, and 0.5 parts ammonium hydroxide giving a glass which was crystallized from ethanol/acetone at −60° C. to give the hydrochloride salt. The title product was collected in an amount of 0.37 g (16%) and had a melting point of 95°-102° C.

MS calculated: 365; observed, 365.

Combustion analysis for $C_{16}H_{24}N_6O_4 \cdot HCl \cdot \frac{1}{2}H_2O$:
Calculated: C, 46.88; H, 6.39; N, 20.50; Cl, 8.65.
Found: C, 46.72; H, 6.34; N, 19.84; Cl, 8.14.

EXAMPLE 3

Cis-N-[1-[3-(4-fluorophenoxy)propyl]-3-methoxy-4-piperidinyl]adenosine

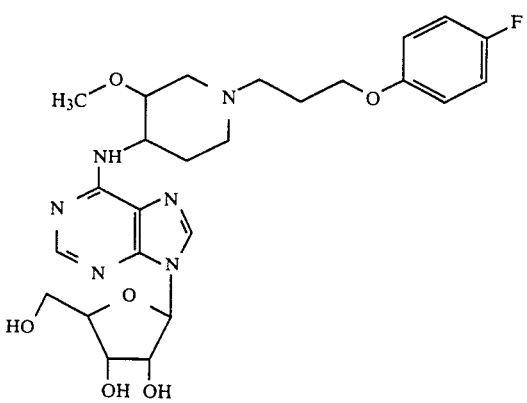

The experiment of Example 1 was repeated in every essential detail with the following exceptions. A suspension was formed using 1.25 g (4.43 mmol) of 6-chloropurine riboside in 15 ml of absolute ethanol. The amine (made in accordance with the teachings of European patent 76530) having the following structure was added in an amount of 1.25 g (4.43 mmol), along with 0.67 g (6.6 mmol) of triethylamine.

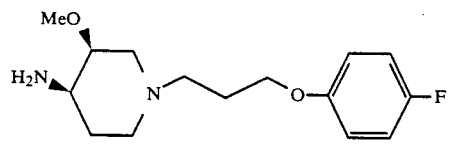

The reaction mixture was refluxed for 96 hours. The resulting residue was separated by chromatography on silica gel eluting with a mixture of 10 parts MeOH (NH$_3$) and 90 parts dichloromethane. The title product was yielded in an amount of 1.5 g (64%) and had a melting point of 77°–87°. MS: Calculated, 533; observed, 533.

Combustion analysis for $C_{25}H_{33}N_6O_6F$: Calculated: C, 56.38; H, 6.25; N, 15.78; F, 3.57. Found: C, 56.36; H, 6.34; N, 15.40; F, 3.40.

EXAMPLE 4 endo-N-(8-methyl-8-azabicyclo[3.2.1]octan-3-yl)adenosine, monohydrochloride

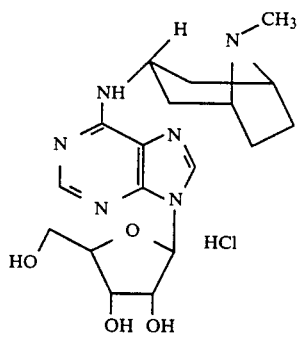

The experiment of Example 1 was repeated in every essential detail with the following exceptions. A suspension of 2.00 g (6.98 mmol) of 6-chloropurine riboside and 14 ml of absolute ethanol was formed. To the suspension was added 0.98 g (6.98 mmol) of an amine having the following structure [produced in accordance with the procedure in J. Am. Chem. Soc. 79, 4194 (957)]

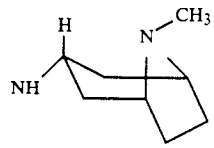

and 0.85 g (8.37 mmol) of triethylamine. The reaction mixture was refluxed for 96 hours. The reaction mixture after heating was a thick suspension which was cooled to room temperature and filtered, washed with absolute ethanol, and dried to yield 2.6 g (87%) of the named product having a melting point of 261°–262°.

MS: Calculated, 391; observed, 391.

Combustion analysis for $C_{18}H_{26}N_6O_4 \cdot HCl$: Calculated: C, 50.64; H, 6.37; N, 19.69; Cl, 8.30. Found: C, 50.62; H, 6.42; N, 19.57; Cl, 8.38.

EXAMPLE 5

N-[2-(1-piperidinyl)ethyl]adenosine

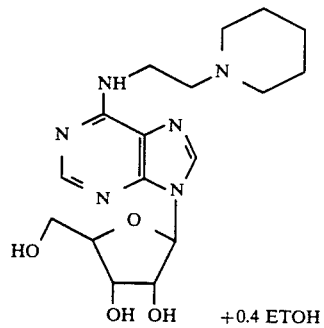

The experiment of Example 1 was repeated in every essential detail except for the following. The suspension was prepared using 2.0 g (6.98 mmol) of the 6-chloropurine riboside in 30 ml of absolute ethanol. 1-(2-Aminoethyl) piperidine (commercially available) was added in an amount of 1.07 g (0.7 ml, 8.3 mmol). Also added to this suspension was 1.5 ml (10.5 mmol) of triethylamine. The reaction mixture was refluxed for 72 hours. The resulting residue was chromatographed on a silica gel column eluting with an eluent of 20 parts methanol, 79 parts dichloromethane and one part ammonium hydroxide. The title product was produced in a yield of 1.1 g (42%).

MS: Calculated, 379; observed, 379.

Combustion analysis for $C_{17}H_{26}N_6O_4 \cdot 0.4EtOH$; Calculated: C, 53.87; H, 7.21; N, 21.18. Found: C, 53.68; H, 7.22; N, 21.15.

EXAMPLE 6 exo-N-(8-methyl-8-azabicyclo[3.2.1]octan-3-yl)adenosine, monohydrochloride

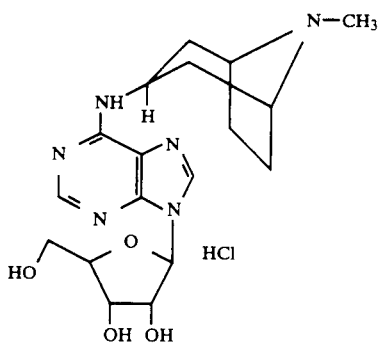

The experiment of Example 1 was repeated in every essential detail with the exception of the following. A suspension was formed containing 2.0 g of 6-chloropurine riboside (6.98 mmol) in 30 ml of absolute ethanol. To the suspension was added 1.17 g (8.37 mmol) of an amine having the following structure (formed in accordance with the procedure described in Berichte 31, 1202 (1898))

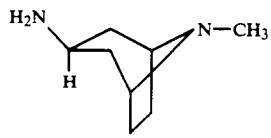

and 1.5 ml (10.5 mmol) of triethylamine. The reaction mixture was refluxed for 90 hours. The reaction mixture after reflux was a thick suspension which was cooled to room temperature and filtered, washed with absolute ethanol, and dried to give 2.2 g of the desired product (74% yield), M.P. 153°-171° C.

MS: Calculated, 395; observed, 395.

Combustion analysis for $C_{18}H_{26}N_6O_4 \cdot HCl$ Calculated: C, 50.64; H, 6.37; N, 19.69; Cl, 8.30. Found: C, 49.82; H, 6.47; N, 19.16; Cl, 8.12.

EXAMPLE 7

N-[2-(2,5-dihydro-1H-pyrrol-1-yl) ethyl]adenosine, monohydrochloride

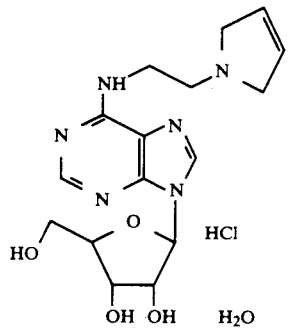

To a suspension of 6 chloropurine riboside (1.27 g, 4.42 mmol) in 10 ml of absolute ethanol was added 2-(2,5-dihydro-1H-pyrrol-1-yl)-1-ethanamine (prepared in accordance with Arzneim. Forsch. 21 (12) 2089 (1971)) in an amount of 0.54 g (4.9 mmol). The reaction mixture was heated under reflux for 40 hours. Concentration of the reaction mixture in vacuo gave a residue which was chromatographed on cellulose powder (Whatman CC 31). The eluent was 85 parts n-butanol and 15 parts water. Fraction monitoring was accomplished by thin layer chromatography on silica gel (Kieselgel 60 F254) eluting with a mixture of 20 parts methanol, 79 parts methylene chloride and one part ammonium hydroxide. The chromatography gave a glass which was azeotroped with water 3 times to remove the n butanol. Lyophilization of the aqueous solution gave the title compound in an amount of 0.41 g (21g yield) as a white powder (mp 88°-105° C.)

MS MH+ Calculated: 363, found 363.

Combustion analysis for $C_{16}H_{22}N_6O_4 \cdot HCl \cdot H_2O$ Calculated: C, 46.10; H, 6.05; N, 20.16; Cl, 8.50. Found: C, 46.35; H, 5.82; N, 20.28; Cl, 8.95.

EXAMPLE 8

N-[2-(1H-imidazol-1-yl)ethyl]adenosine, hydrochloride

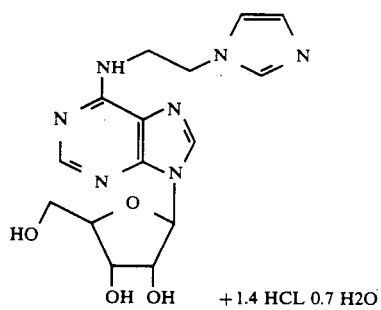

To a suspension of 6-chloropurine riboside (1.63 g, 5.69 mmol) in 12 ml of absolute ethanol was added 0.63 g (5.7 mmol) of 2-(imidazol-1-yl)ethylamine (prepared in accordance with Z.Obsch. Chem. 9 1933 (1939); Chem Ab. 1940 2466) plus 0.80 g (8.0 mmol) of triethylamine. The reaction mixture was heated under reflux for 77 hours. Removal of the solvent in vacuo and chromatography of the residue on silica gel eluting with a mixture of MeOH (NH3) and dichloromethane in a ratio of 14:86 gave the free base of the title compound in an amount of 1.2 g (59% yield). The material was converted to the hydrochloride salt by suspending the material in 20 ml of water at 0° centigrade and adding 1N hydrochloric acid until a pH of 2.6 was attained. The solution was frozen and lyophilized to a white powder which was passed through a column of cellulose powder eluting with a mixture of 85 parts n-butanol and 15 parts water. The appropriate fractions were combined and concentrated to give a glass which was azeotroped twice with water and then dissolved in water, frozen and lyophilized yielding 0.97 g of the title compound (41% yield) as a white powder.

MS: MH+ Calculated: 362 Found: 362

Combustion analysis for $C_{15}H_{19}N_7O_4 \cdot 1.4HCl \cdot 0.7H_2O$ Calculated: C, 42.39; H, 5.17; N, 23.07; Cl, 11.68. Found: C, 42.34; H, 5.05; N, 23.58; Cl, 11.81.

EXAMPLE 9

N-[2-(2-methyl-1H-imidazol-1-yl) ethyl]adenosine, hydrochloride

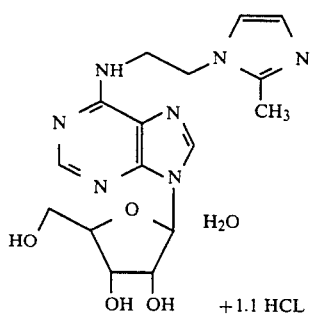

+1.1 HCL

A suspension was prepared containing 1.64 g (5.74 mmol) of 6-chloropurine riboside in 12 ml of absolute ethanol. To the solution was added 0.72 g (5.7 mmol) of 2-(2-methyl-imidazol-1-yl) ethylamine (prepared in accordance with Z.Obsch. Chim. 11, 545 (1941); Chem Ab. 1941 6938) and 0.81 g (8.0 mmol) of triethylamine. The reaction mixture was heated under reflux for 77 hours. The solvent was removed in vacuo and chromatography of the residue on silica gel was performed by eluting with a mixture of 22 parts methanol, 88 parts methylene chloride, and one part ammonium hydroxide. The title compound was obtained as the free base yielding 1.2 g (55% yield). This material was converted to the hydrochloride salt by suspending in 20 ml of water at 0° and adding 1 normal hydrochloric acid until a pH of 2.6 was attained. The solution was frozen and lyophilized giving a white powder which was passed through a column of cellulose powder eluting with a mixture of 85 parts n-butanol and 15 parts water. The appropriate fractions were combined and concentrated to give a glass which was azeotroped twice with water and then dissolved in water, frozen and lyophilized giving 1.1 g (44% yield) of the title compound as a white powder.

MS: MH+ Calculated: 376 Found: 376

Combustion analysis for $C_{16}H_{21}N_7O_4 \cdot 1.1HCl \cdot H_2O$ Calculated: C, 44.33; H, 5.60; N, 22.62; Cl, 8.45 Found: C44.18; H, 5.27; N, 22.79; Cl: 9.21.

The compounds herein have been shown to be useful for treating gastrointestinal motility disorders in mammals. Their utility has been shown by their demonstrated prokinetic activity. Prokinetic activity of any compound can be determined by measuring the enhancement of gastric emptying of a meal in a rat model to which the compound has been administered. This method for determining the prokinetic activity of a compound has been described by Droppleman, et al, J. Pharmacol. and Methods 4: 227–230 (1980).

RAT GASTRIC EMPTYING PROTOCOL

A test meal for measuring gastric emptying in rats was prepared. Ten grams of methylcellulose (2 g solution, 15 centipoises, Aldrich Chemical Company, Milwaukee, Wis.) was added to 200 ml of cold water and mixed at 20,000 rpm in a Waring blender to insure dispersion and hydration of the methylcellulose. In addition, two beef bouillon cubes (Wyler's, Columbus, Ohio) dissolved in 100 ml of warm water were added to the mixture, followed by 16 g of casein (Hammersten, Schwartz/Mann, Orangeburg, N.Y.), 8 g of powdered confectioners sugar and 8 g of cornstarch. The ingredients were mixed for two minutes at 20,000 rpm and the resultant test meal was refrigerated for 48 hours to allow trapped air to escape. Male Charles River Rats, Crl: COBS, CD (SD) BR Strain, 180–200 g body weight, were used in groups of six animals. The animals were food deprived for 24 hours prior to the experiment with access to water ad libitum. The compounds to be evaluated were prepared in a 0.5% aqueous methylcellulose solution. If insoluble, the mixture was homogenized for two minutes at 5500 rpm using a Try-R-Stir-R. The compounds were injected intraperitoneally at a volume of 5 ml/kg, 30 minutes before the test meal, (3.0 ml/rat i.g.). Control animals received only the vehicle. Sixty minutes after the test meal, the rats were sacrificed by cervical dislocation. The stomachs were removed intact and weighed. The stomachs were kept opened, gently rinsed with tap water, blotted dry with paper towelling, and the empty stomach weighed. The difference between the weight of the full and empty gtomach is indicative of the amount of meal remaining in the stomach. The amount of meal remaining in the stomach was subtracted from the weight of 3 ml of the test meal to determine the amount of food emptied from the stomach during the test. Weight of the test meal was determined by weighing three samples (3 ml) at the beginning and three samples at the end of each experiment and calculating the mean. The mean and standard error of the amount of meal emptied were calculated.

A dose of compound was considered active if emptying in 4 of 6 animals given the compound exceeded the median amount emptied for the control animals. These compounds were then tested for antral motor effects in conscious dogs.

ANTRAL MOTILITY IN CONSCIOUS FASTED DOGS

Gastric antral contractile activity is stimulated by prokinetic drugs which enhance gastric emptying of solid food as has been shown by Jacoby et al, Gastroenterology, 52 676–684 (1967). This contractile activity is thought to enhance gastric emptying by more rapidly reducing food particle size for passage through the pylorus. The ability of a test compound to increase the frequency and/or amplitude of the contractile activity is a measure of gastrointestinal prokinetic activity of the compound.

Mongrel dogs of either sex were surgically implanted with strain gauge force transducers on the gastric antrum at 6 cm, 4 cm and 2 cm from the gastroduodenal junction. The dogs were allowed at least two weeks to recover and were trained to stand quietly in Pavlov slings.

Dogs were fasted for 18 to 24 hours prior to each experiment to record a pattern of antral contractile activity characteristic of the fasted state called the Migrating Motor Complex (MMC). The period of the MMC cycle is approximately 90 to 120 minutes and consists of 45 to 60 minutes of motor quiescence (Phase I) 30 to 45 minutes of intermittent activity (Phase II) and 10 to 15 minutes of intense contractile activity (Phase III). A control MMC period is recorded prior to compound administration to obtain the length of the quiescent Phase I period. Compound is given intravenously at the end of Phase III of the control MMC cycle and a subsequent Phase I period is examined for the ability of the compound to produce contractions of a determined duration.

Table I provides the results of the rat gastric emptying evaluation and the dog fasted antral motility evaluation of representative compounds herein. In the table, the indicated result for the rat gastric emptying is the percentage increase in gastric emptying at a dose of 10 milligrams per kilogram (mpk) administered intraperitoneally (IP). The metoclopramide value at 10.0 mpk (IP) is the value given in parentheses in the Table. The results for the dog fasted antral motility study are reported as the dose in milligrams per kilogram (mpk) administered intravenously and the duration in minutes of antral motility. The data in Table I reported for the rat gastric emptying study for Examples 7 and 9 were conducted at a dose of 3 milligrams per kilogram.

TABLE I

| Example No. of Compound | Rat Gastric Emptying | Dog Fasted Antral Motility Dose (mpk) | Duration |
|---|---|---|---|
| 1 | −7.1 | — | — |
| 2 | 24.3 | (30.8) | — | — |
| 3 | 2.0 | (30.0) | — | — |
| 4 | 16.7 | (43.1) | 3.0 | 49 min. |
|   |      |        | 10.0 | 60 min. |
| 5 | 14.3 | (30.0) | — | — |
| 6 | 15.1 | — | 3.0 | 52 min. |
|   |      |   | 10.0 | 60 min. |
| 7 | 15.5 | (17.0) | 3.0 | 60 min. |
| 8 | 20.2 | (14.0) | 0.3 | 35 min. |
|   |      |        | 3.0 | 60 min. |
| 9 | 6.7 | (14.0) | 3.0 | 60 min. |

What is claimed is:
1. A compound of the formula

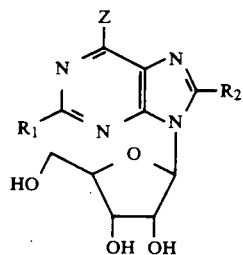

or a pharmaceutically acceptable salt thereof, wherein Z can be:

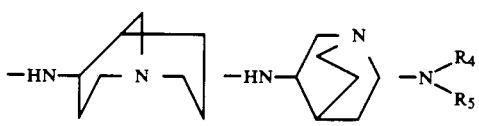

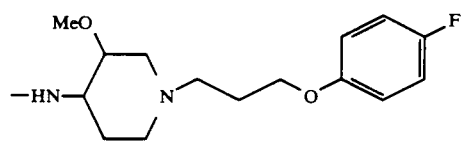

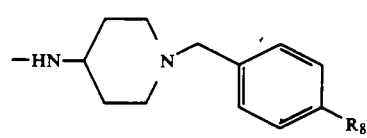

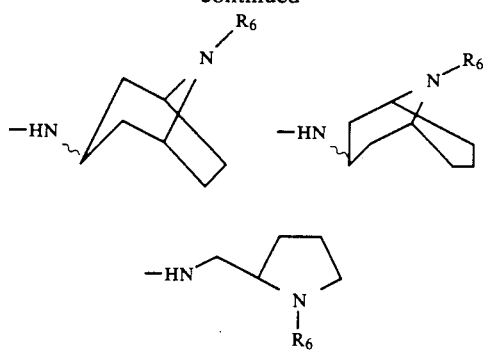

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl or phenyl;

wherein $R_4$ can be hydrogen or alkyl wherein $R_5$ is —X—Y wherein X can be a straight chain, branched chain or cyclic alkylene from 1 to 10 carbon atoms, and wherein Y can be optionally substittued imidazol-1-yl, imidazol-2-yl, pyrrolinyl, pyrrolidinyl, piperidinyl, triazolyl,

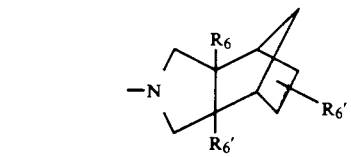

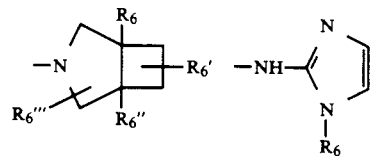

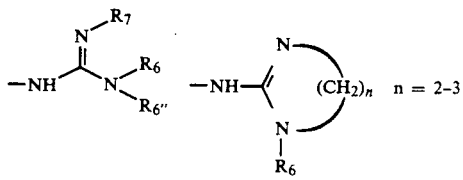

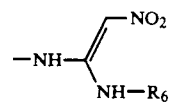

wherein $R_8$ can be hydrogen, alkyl, aralkyl, aryl or acyl; and wherein $R_6$ can independently be hydrogen, alkyl, aralkyl, phenyl, and optionally substituted phenyl and aralkyl;

wherein $R_7$ can be hydrogen, alkyl, aralkyl, phenyl, cyano and nitro; and wherein n can be 2 or 3.

2. A compound as recited in claim 1 wherein Z is

3. A compound as recited in claim 2 wherein R₅ is —X—Y and X is a straight chain alkylene group having from 1 to 10 carbon atoms.

4. A compound as recited in claim 3 wherein Y can be

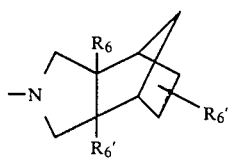

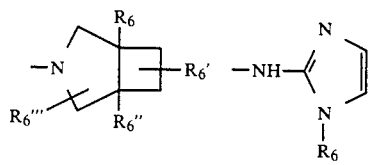

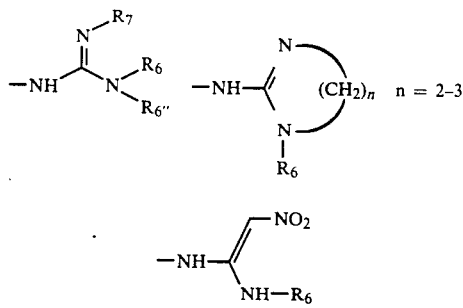

5. A compound as recited in claim 3 wherein Y can be imidazol-1-yl, imidazol-2-yl, pyrrolinyl, pyrrolidinyl, piperidinyl, and triazolyl.

6. A compound as recited in claim 3 wherein R₁ and R₂ are hydrogen.

7. A compound as recited in claim 6 wherein R₆ is hydrogen.

8. A compound as recited in claim 6 wherein R₆ is methyl.

9. A compound as recited in claim 1 wherein Z can be:

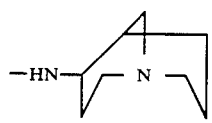 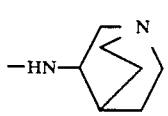

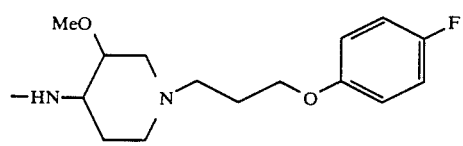

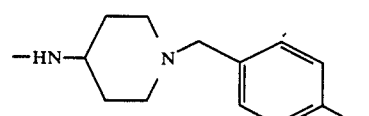

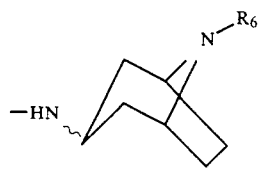

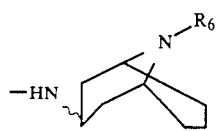 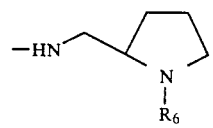

wherein R₁ and R₂ are independently hydrogen, hydroxyl, halogen, alkyl, phenyl, alkoxy, morpholino, piperidino, piperazino, phenoxy, thiophenoxy or amino optionally substituted by alkyl, aralkyl or phenyl;

wherein R₈ can be hydrogen, alkyl, aralkyl, aryl or acyl; and wherein R₆ can be hydrogen, alkyl, aralkyl, phenyl, and optionally substituted phenyl and aralkyl; or a pharmaceutically acceptable salt thereof.

10. A compound as recited in claim 9 wherein R₁ and R₂ are hydrogen.

11. A compound as recited in claim 10 wherein R₆ is hydrogen.

12. A compound as recited in claim 10 wherein R₆ is methyl.

13. A compound as recited in claim 10 wherein is methyl.

14. A compound as recited in claim 1 having the structure

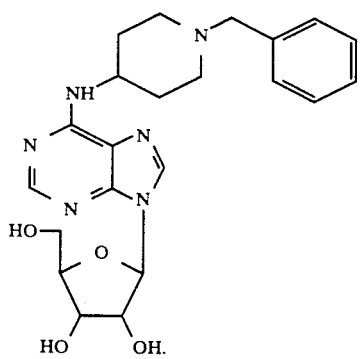

15. A compound as recited in claim 1 having the structure

16. A compound as recited in claim 1 having the structure
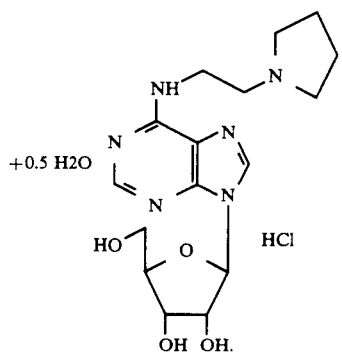
+0.5 H2O
17. A compound as recited in claim 1 having the structure
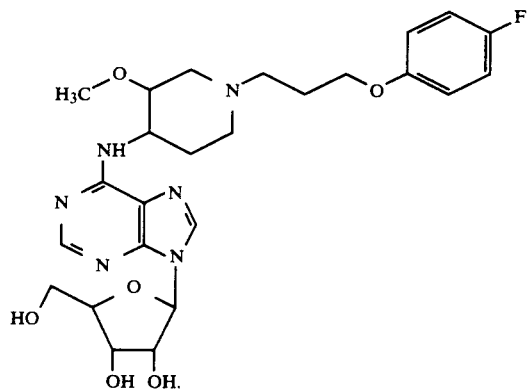
18. A compound as recited in claim 1 having the structure
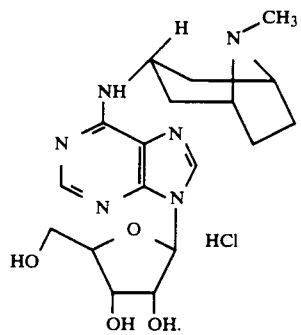
19. A compound as recited in claim 1 having the structure
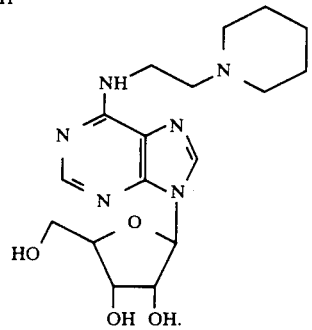
+0.4 ETOH
20. A compound as recited in claim 1 having the structure
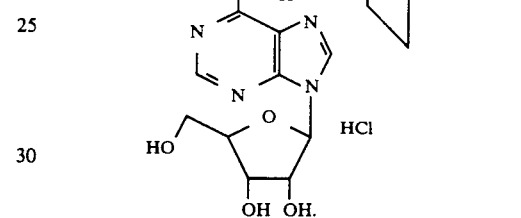
21. A compound as recited in claim 1 having the structure
+1.4 HCL 0.7 H2O
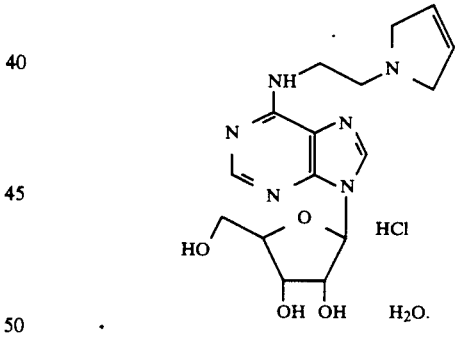
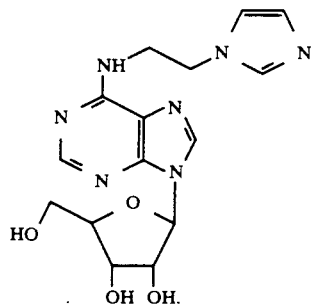

22. A compound as recited in claim 1 having the structure

+1.1 HCL

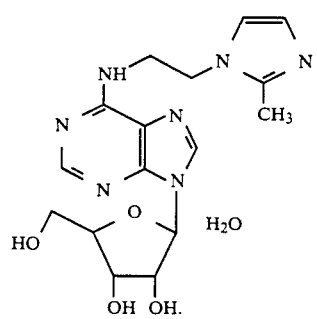

23. A pharmaceutical composition for the treatment of gastrointestinal motility disorders comprising a therapeutically effective amount of a compound of the formula

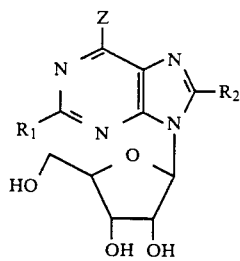

or a pharmaceutically acceptable salt thereof. wherein Z can be:

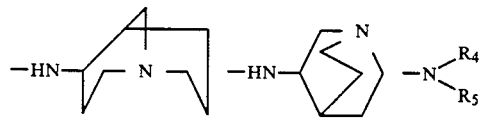

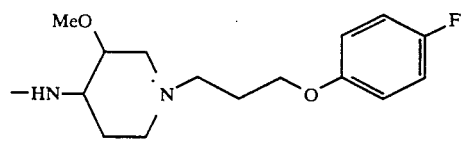

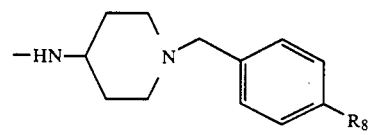

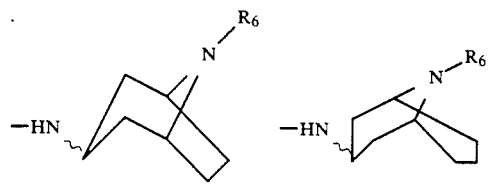

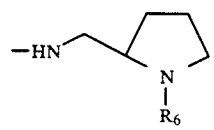

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl or phenyl;

wherein $R_4$ can be hydrogen or alkyl wherein $R_5$ is —X—Y wherein X can be a straight chain, branched chain or cyclic alkylene from 1 to 10 carbon atoms, and wherein Y can be optionally substituted imidazol-1-yl, imidazol-2-yl, pyrrolinyl, pyrrolidinyl, piperidinyl, triazolyl,

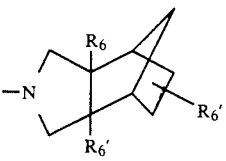

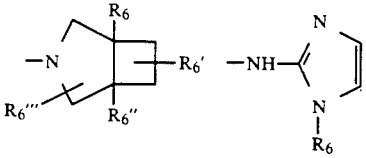

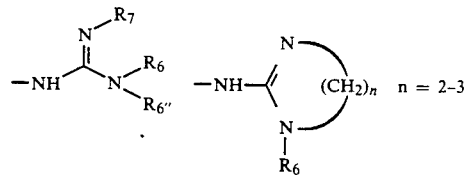

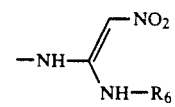

wherein $R_8$ can be hydrogen, alkyl, aralkyl, aryl or acyl;

wherein $R_6$ can independently be hydrogen, alkyl, aralkyl, phenyl, and optionallg substituted phenyl and aralkyl; and wherein $R_7$ can be hydrogen, alkyl, aralkyl, phenyl, cyano and nitro;

wherein n can be 2 or 3; and a pharmaceutically acceptable carrier.

24. A pharmaceutical composition as recited in claim 23 wherein Z is

25. A pharmaceutical composition as recited in claim 24 wherein $R_5$ is —X—Y and X is a straight chain alkylene group having from 1 to 10 carbon atoms.

26. A pharmaceutical composition as recited in claim 25 wherein Y can be

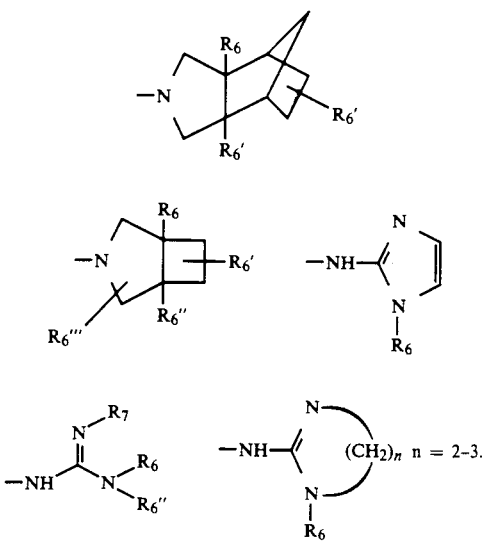

wherein $R_1$ and $R_2$ are independently hydrogen, hydroxyl, halogen, alkyl, phenyl, alkoxy, morpholino, piperidino, piperazino, phenoxy, thiophenoxy or amino optionally substituted by alkyl, aralkyl or phenyl;

wherein $R_8$ can be hydrogen, alkyl, aralkyl, aryl or acyl; and wherein $R_6$ can independently be hydrogen, alkyl, aralkyl, phenyl, and optionally substituted phenyl and aralkyl; and a pharmaceutically acceptable carrier.

33. A pharmaceutical composition as recited in claim 32 wherein $R_1$ and $R_2$ are hydrogen.

27. A pharmaceutical compositon as recited in claim 25 wherein Y can be imidazol-1-yl, imidazol-2-yl, pyrrolinyl, pyrrolidinyl, piperidinyl, and triazolyl.

28. A pharmaceutical composition as recited in claim 25 wherein $R_1$ and $R_2$ are hydrogen 29. A pharmaceutical composition as recited in claim 28 wherein $R_6$ is hydrogen.

30. A pharmaceutical composition as recited in claim 28 wherein $R_6$ is methyl.

31. A pharmaceutical composition as recited in claim 28 wherein $R_8$ is methyl.

32. A pharmaceutical composition as recited in claim 23 wherein Z can be:

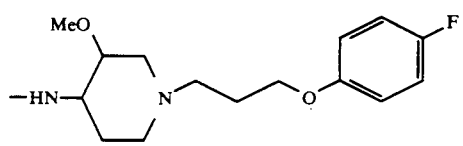

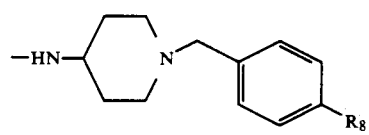

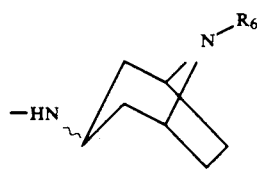

34. A pharmaceutical composition as recited in claim 33 wherein $R_6$ is hydrogen.

35. A pharmaceutical composition as recited in claim 33 wherein $R_6$ is methyl.

36. A pharmaceutical composition as recited in claim 33 wherein $R_8$ is methyl.

37. A pharmaceutical composition as recited in claim 23 wherein the compound has the structure

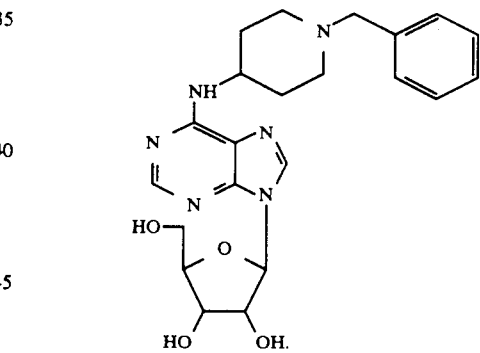

38. A pharmaceutical composition as recited in claim 23 wherein the compound has the structure

+0.5 H2O

39. A pharmaceutical composition as recited in claim 23 wherein the compound has the structure

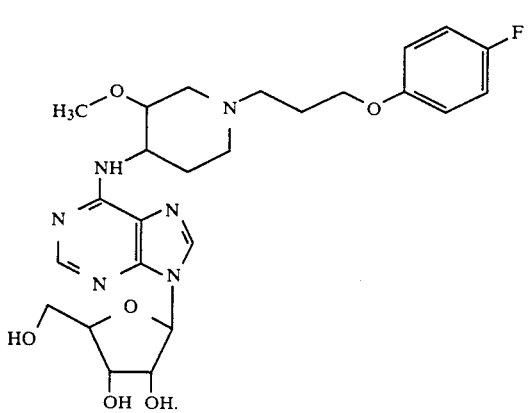

40. A pharmaceutical composition as recited in claim 23 wherein the compound has the structure

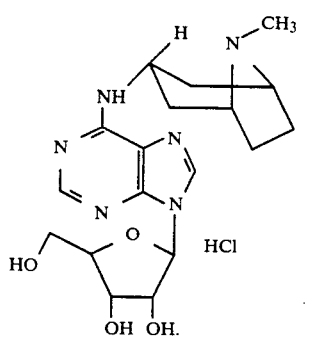

41. A pharmaceutical composition as recited in claim 23 wherein the compound has the structure

+0.4 ETOH

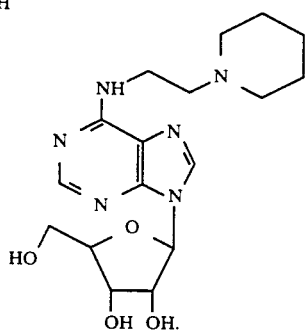

42. A pharmaceutical composition as recited in claim 23 wherein the compound has the structure

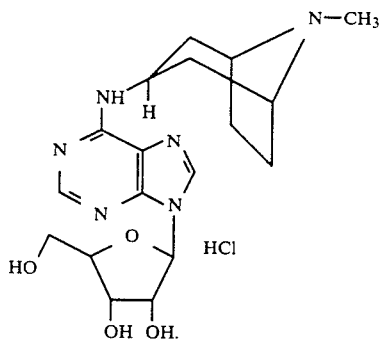

43. A pharmaceutical composition as recited in claim 23 wherein the compound has the structure

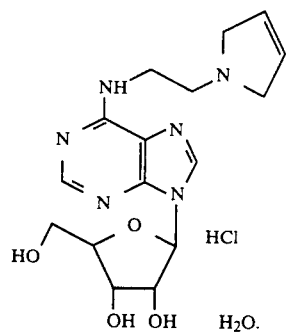

44. A pharmaceutical composition as recited in claim 23 wherein the compound has the structure

+1.4 HCL 0.7 H2O

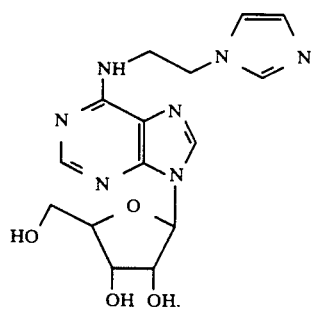

45. A pharmaceutical composition as recited in claim 23 wherein the compound has the structure

+1.1 HCL

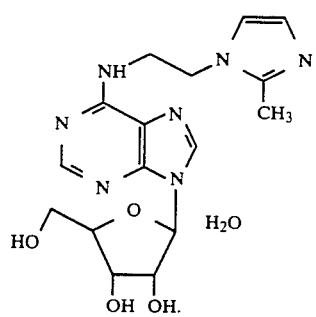

* * * * *

UNITED STATES PATENT AND TRADEMARK OFFICE
CERTIFICATE OF CORRECTION

PATENT NO. : 5,055,569

DATED : October 8, 1991

INVENTOR(S) : Becker et al

It is certified that error appears in the above-identified patent and that said Letters Patent is hereby corrected as shown below:

Column 1, line 26, reading "anti hypertensive" should read -- anti-hypertensive --

Column 1, line 26, reading "anti allergic" should read -- anti-allergic --

Column 1, line 27, reading "anti hyper-lipaemic" should read -- anti-hyper lipaemic --

Column 1, line 37, reading "anti hypertensive" should read -- anti-hypertensive --

Column 1, line 42, reading "K Kikugawa" should read -- K. Kikugawa --

Column 1, line 56, reading "anti" should read -- anti- --

Column 1, line 60, reading "anti" should read -- anti- --

Column 1, line 64, reading "anti lipolytic" should read -- anti-lipolytic --

Column 2, the last structure, reading

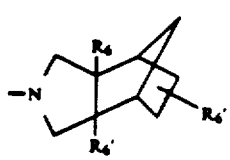   should read   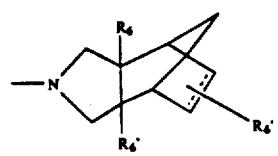

UNITED STATES PATENT AND TRADEMARK OFFICE
CERTIFICATE OF CORRECTION

PATENT NO. : 5,055,569
DATED : October 8, 1991
INVENTOR(S) : Becker et al

It is certified that error appears in the above-identified patent and that said Letters Patent is hereby corrected as shown below:

Column 4, the structure at line 33, reading

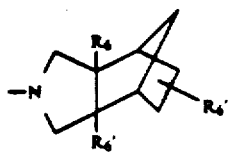     should read     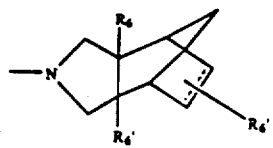

Column 5, line 29, reading "peperidinyl," should read -- piperidinyl --

Column 5, the structure at line 35, reading

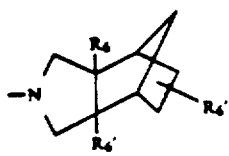     should read     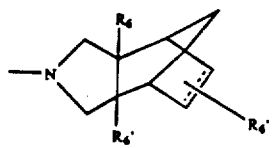

Column 5, line 63, reading "R" should read -- $R_7$ --

Column 7, line 3, reading "cis and trans isomers" should read -- cis- and trans-isomers --

UNITED STATES PATENT AND TRADEMARK OFFICE
CERTIFICATE OF CORRECTION

PATENT NO. : 5,055,569

DATED : October 8, 1991

INVENTOR(S) : Becker et al

It is certified that error appears in the above-identified patent and that said Letters Patent is hereby corrected as shown below:

Column 7, line 35, reading "iso propyl" should read -- iso-propyl --

Column 7, line 66, reading "elixers" should read -- elixirs --

Column 9, line 2, reading "obtained" should read -- obtained. --

Column 9, line 67, reading "rgboside" should read -- riboside --

Column 10, line 48, reading "Aminoethyl) pyrrolidine" should read -- Aminoethyl)-pyrrolidine --

Column 12, line 5, reading "(957)]" should read --(1957)] --

Column 12, line 66, reading "EtOH;" should read -- EtOH: --

Column 13, line 64, reading "6 chloropurine" should read -- 6-chloropurine --

Column 14, line 11, reading "n butanol." should read -- n-butanol. --

Column 14, line 12, reading "(21g yield)" should read -- (21% yield) --

Column 15, line 60, reading "(2 g solu-" should read -- (2% solu- --

Column 16, line 22, reading "gtomach" should read -- stomach --

UNITED STATES PATENT AND TRADEMARK OFFICE
CERTIFICATE OF CORRECTION

PATENT NO. : 5,055,569

DATED : October 8, 1991

INVENTOR(S) : Becker et al

It is certified that error appears in the above-identified patent and that said Letters Patent is hereby corrected as shown below:

Column 18, line 23, reading "wherein $R_5$is" should read -- wherein $R_5$ is --

Column 18, line 26, reading "substittued" should read -- substituted --

Column 18, structure at line 35, reading

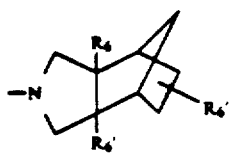     should read     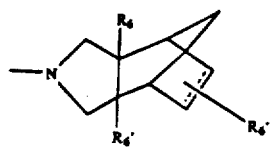

Column 19, structure at line 15, reading

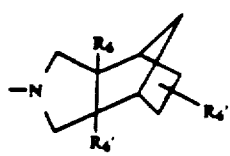     should read     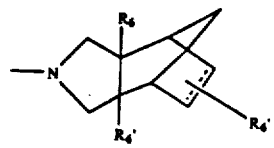

Column 20, line 43, reading "wherein is" should read -- wherein $R_8$ is --

UNITED STATES PATENT AND TRADEMARK OFFICE
CERTIFICATE OF CORRECTION

PATENT NO. : 5,055,569

DATED : October 8, 1991

INVENTOR(S) : Becker et al

It is certified that error appears in the above-identified patent and that said Letters Patent is hereby corrected as shown below:

Column 23, line 34, reading "salt thereof" should read -- salt thereof, --

Column 24, structure at line 20, reading

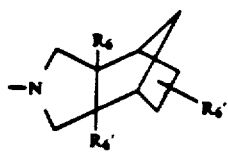   should read   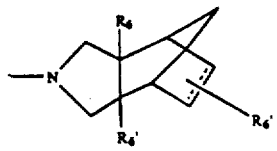

Column 24, line 48, reading "optionallg" should read -- optionally --

Column 25, structure at line 5, reading

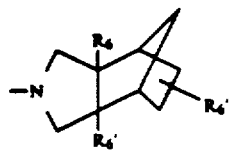   should read   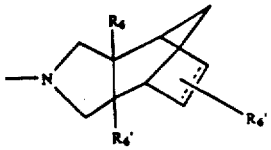

Column 25, line 25, reading "compositon" should read -- composition --

UNITED STATES PATENT AND TRADEMARK OFFICE
CERTIFICATE OF CORRECTION

PATENT NO. : 5,055,569

DATED : October 8, 1991

INVENTOR(S) : Becker et al

It is certified that error appears in the above-identified patent and that said Letters Patent is hereby corrected as shown below:

Column 25, line 30, reading "are hydrogen" should read -- are hydrogen. --

Signed and Sealed this

Ninth Day of November, 1993

*Attest:*

BRUCE LEHMAN

*Attesting Officer*     Commissioner of Patents and Trademarks